US010957452B2

(12) United States Patent
Stevens et al.

(10) Patent No.: US 10,957,452 B2
(45) Date of Patent: Mar. 23, 2021

(54) THERAPY RECOMMENDATION

(71) Applicant: International Business Machines Corporation, Armonk, NY (US)

(72) Inventors: Richard J. Stevens, Monkton, VT (US); Corey Sanders, Dublin, OH (US); Fernando Jose Suarez Saiz, Armonk, NY (US); Michael Britt, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 203 days.

(21) Appl. No.: 16/021,401

(22) Filed: Jun. 28, 2018

(65) Prior Publication Data

US 2020/0005939 A1 Jan. 2, 2020

(51) Int. Cl.
*G16H 50/20* (2018.01)
*G16H 80/00* (2018.01)
*G16H 20/30* (2018.01)
*G16H 10/20* (2018.01)
*G16H 15/00* (2018.01)
(Continued)

(52) U.S. Cl.
CPC ............. *G16H 50/20* (2018.01); *G16H 10/20* (2018.01); *G16H 20/30* (2018.01); *G16H 80/00* (2018.01); *G16H 10/60* (2018.01); *G16H 15/00* (2018.01); *G16H 50/70* (2018.01)

(58) Field of Classification Search
CPC .. G06F 16/20; G06F 16/243; G06F 16/24578; G06F 16/30; G06F 16/3329; G06F 16/3344; G06F 40/30; G06N 5/02; G06N 20/00; G06Q 10/0631; G06Q 10/10; (Continued)

(56) References Cited

U.S. PATENT DOCUMENTS 7,805,385 B2 * 9/2010 Steck .................. G06F 19/00
706/10
8,583,380 B2 11/2013 Stephan et al.
(Continued)

OTHER PUBLICATIONS

Fiszman, Marcelo, et al. "Interpreting Comparative Constructions in Biomedical Text". University of Tennessee. Jun. 2017. (Year: 2017).*
(Continued)

*Primary Examiner* — Jonathan Durant
*Assistant Examiner* — Chance L. Smith
(74) *Attorney, Agent, or Firm* — L. Jeffrey Kelly

(57) ABSTRACT

A method, computer program product, and computing system device for receiving, at a computing device, a plurality of candidate therapy options, a corpus of therapy data, and a set of therapy recipient cohorts. At least a portion of therapy data may be filtered from the corpus of therapy data based upon, at least in part, the plurality of candidate therapy options and the set of therapy recipient cohorts. A graph may be generated to include a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. Using the graph, a ranked list of the plurality of candidate therapy options may be generated.

20 Claims, 7 Drawing Sheets

(51) Int. Cl.
  *G16H 50/70* (2018.01)
  *G16H 10/60* (2018.01)
(58) Field of Classification Search
  CPC ........ G16H 10/00; G16H 10/60; G16H 50/20;
       G16H 40/67; G16H 50/30; G16H 50/70
  See application file for complete search history.

(56) References Cited

U.S. PATENT DOCUMENTS

| | | | | |
|---|---|---|---|---|
| 8,655,682 | B2* | 2/2014 | Srivastava | G06Q 50/22 705/3 |
| 9,336,205 | B2* | 5/2016 | Moilanen | G06F 40/211 |
| 2006/0277465 | A1* | 12/2006 | Pandit | G06F 40/289 715/234 |
| 2008/0082359 | A1* | 4/2008 | Jung | G06Q 10/10 705/2 |
| 2009/0299766 | A1 | 12/2009 | Friedlander et al. | |
| 2013/0035956 | A1* | 2/2013 | Carmeli | G06Q 10/10 705/3 |
| 2015/0046191 | A1 | 2/2015 | Futscher de Deus et al. | |
| 2016/0063212 | A1 | 3/2016 | Monier et al. | |
| 2016/0188813 | A1 | 6/2016 | Hennenfent | |
| 2018/0322252 | A1* | 11/2018 | Eggebraaten | G06F 19/3481 |
| 2019/0130069 | A1* | 5/2019 | Li | G16H 10/60 |

OTHER PUBLICATIONS

Kohn, M. S., et al. "IBM's Health Analytics and Clinical Decision Support". IMIA Yearbook of Medical Informatics. Aug. 15, 2014 (Year: 2014).*
Catalá-López, Ferrán, et al. "Network meta-analysis for comparing treatment effects of multiple interventions: an introduction". Rheumatol Int. Apr. 2, 2014. (Year: 2014).*
Hristovski et al., "Using Literature-Based discovery to Identify Novel Therapeutic Approaches," Cardiovascular & Hematological Agents in Medicinal Chemistry, 2012, 10, 000-000, pp. 1-11.
Sterne et al., "Publication and Related Bias in Meta-Analysis: Power of Statistical Tests and Prevalence in the Literature," Journal of Clinical Epidemiology 53 (2000) 1119-1129.
Mills et al., "How to Use an Article Reporting a Multiple Treatment Comparison Meta-Analysis," Users Guide to the Medical Literature, JAMA, Sep. 26, 2012, vol. 308, No. 12., pp. 1246-1253.

* cited by examiner

500

| Most Preferred Therapy Options | 302 (represented by node 502), 310 (represented by node 510) |
| --- | --- |
| Next Preferred Therapy Options | 304 (represented by node 504), 306 (represented by node 506) |
| Least Preferred Therapy Option | 308 (represented by node 508), 312 (represented by node 512) |

524

THERAPY RECOMMENDATION

BACKGROUND

Current treatment advisor implementations are often driven by the opinions of a very small number of doctors (e.g., 1-2), where therapies are ranked based on the explicit input of those specific physicians. Evidence may be associated with therapy recommendations, but does not play a role in determining what therapy options are considered best, next best, and not recommended therapy options. Conventional systems for therapy recommendations may, therefore, be biased towards the specific physicians providing input and may not reflect general consensus of best therapy options for a given disease. The fact that recommendations are not evidence-based has led to a significant number of prospective clients avoiding use of these solutions given lack of agreement with recommendation bias from a given, potentially competing organization. Significant manual effort is required to capture physician input relative to how to rank therapies for a given patient cohort, effort that must be repeated on a frequent basis to remain current with latest advances in treatments for a given disease.

BRIEF SUMMARY OF DISCLOSURE

In one example implementation, a computer-implemented method is executed on a computing device and may include but is not limited to receiving, at a computing device, a plurality of candidate therapy options, a corpus of therapy data, and a set of therapy recipient cohorts. At least a portion of therapy data may be filtered from the corpus of therapy data based upon, at least in part, the plurality of candidate therapy options and the set of therapy recipient cohorts. A graph may be generated to include a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. Using the graph, a ranked list of the plurality of candidate therapy options may be generated.

One or more of the following example features may be included. Filtering the at least a portion of therapy data from the corpus of therapy data may include identifying, from the corpus of therapy data, a set of therapy data that characterizes the plurality of candidate therapy options; receiving a set of criteria indicating usage configurations for the plurality of candidate therapy options; determining, using a set of criteria indicating usage configurations for the one or more candidate therapy options, a subset of the plurality of candidate therapy options for at least a subset of the set of therapy recipient cohorts; and/or determining a subset of the set of therapy data that characterizes the subset of the plurality of therapy options for the at least a subset of the set of therapy recipient cohorts. Generating the graph may include identifying a plurality of outcome statements comparing a plurality of therapy options from the subset of the set of therapy data and defining a sentiment factor for each of the plurality of outcome statements comparing the plurality of therapy options based upon, at least in part, performing sentiment analysis on the plurality of outcome statements data comparing the plurality of therapy options. Generating the ranked list of the plurality of candidate therapy options may include ranking the plurality of candidate therapy options as one or more of: a most positive therapy option, a least positive therapy option, and one or more moderately positive therapy options. A first comparative assessment for a first therapy option with respect to at least a subset of a set of therapy recipient cohorts may be determined based upon, at least in part, comparing the first therapy option of the plurality of candidate therapy options to a reference therapy option. A second comparative assessment for a second therapy option with respect to the at least a subset of the set of therapy recipient cohorts may be determined based upon, at least in part, comparing the second therapy option of the plurality of candidate therapy options to the reference therapy option. A hierarchical order to the first therapy option and the second therapy option may be assigned to generate the ranking of the plurality of candidate therapy options based upon, at least in part, analyzing the first comparative assessment for the first therapy option and the second comparative assessment for the second therapy option. A sentiment factor conflict may be detected with respect to the plurality of connections between a first therapy option and a second therapy option. Using a set of ranking criteria, the plurality of connections between the first therapy option and the second therapy option may be evaluated. A hierarchical order to the first therapy option and the second therapy option may be assigned to generate the ranking of the subset of therapy options based upon, at least in part, evaluating the plurality of connections between the first and second therapy options.

In another example implementation, a computer program product resides on a non-transitory computer readable medium that has a plurality of instructions stored on it. When executed across one or more processors, the plurality of instructions cause at least a portion of the one or more processors to perform operations that may include but are not limited to receiving, at a computing device, a plurality of candidate therapy options, a corpus of therapy data, and a set of therapy recipient cohorts. At least a portion of therapy data may be filtered from the corpus of therapy data based upon, at least in part, the plurality of candidate therapy options and the set of therapy recipient cohorts. A graph may be generated to include a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. Using the graph, a ranked list of the plurality of candidate therapy options may be generated.

One or more of the following example features may be included. Filtering the at least a portion of therapy data from the corpus of therapy data may include identifying, from the corpus of therapy data, a set of therapy data that characterizes the plurality of candidate therapy options; receiving a set of criteria indicating usage configurations for the plurality of candidate therapy options; determining, using a set of criteria indicating usage configurations for the one or more candidate therapy options, a subset of the plurality of candidate therapy options for at least a subset of the set of therapy recipient cohorts; and/or determining a subset of the set of therapy data that characterizes the subset of the plurality of therapy options for the at least a subset of the set of therapy recipient cohorts. Generating the graph may include identifying a plurality of outcome statements comparing a plurality of therapy options from the subset of the set of therapy data and defining a sentiment factor for each of the plurality of outcome statements comparing the plurality of therapy options based upon, at least in part, performing sentiment analysis on the plurality of outcome statements data comparing the plurality of therapy options.

Generating the ranked list of the plurality of candidate therapy options may include ranking the plurality of candidate therapy options as one or more of: a most positive therapy option, a least positive therapy option, and one or more moderately positive therapy options. A first comparative assessment for a first therapy option with respect to at least a subset of a set of therapy recipient cohorts may be determined based upon, at least in part, comparing the first therapy option of the plurality of candidate therapy options to a reference therapy option. A second comparative assessment for a second therapy option with respect to the at least a subset of the set of therapy recipient cohorts may be determined based upon, at least in part, comparing the second therapy option of the plurality of candidate therapy options to the reference therapy option. A hierarchical order to the first therapy option and the second therapy option may be assigned to generate the ranking of the plurality of candidate therapy options based upon, at least in part, analyzing the first comparative assessment for the first therapy option and the second comparative assessment for the second therapy option. A sentiment factor conflict may be detected with respect to the plurality of connections between a first therapy option and a second therapy option. Using a set of ranking criteria, the plurality of connections between the first therapy option and the second therapy option may be evaluated. A hierarchical order to the first therapy option and the second therapy option may be assigned to generate the ranking of the subset of therapy options based upon, at least in part, evaluating the plurality of connections between the first and second therapy options.

In another example implementation, a computing system may include one or more processors and one or more memories, wherein the computing system is configured to perform operations that may include but are not limited to receiving, at a computing device, a plurality of candidate therapy options, a corpus of therapy data, and a set of therapy recipient cohorts. At least a portion of therapy data may be filtered from the corpus of therapy data based upon, at least in part, the plurality of candidate therapy options and the set of therapy recipient cohorts. A graph may be generated to include a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. Using the graph, a ranked list of the plurality of candidate therapy options may be generated.

One or more of the following example features may be included. Filtering the at least a portion of therapy data from the corpus of therapy data may include identifying, from the corpus of therapy data, a set of therapy data that characterizes the plurality of candidate therapy options; receiving a set of criteria indicating usage configurations for the plurality of candidate therapy options; determining, using a set of criteria indicating usage configurations for the one or more candidate therapy options, a subset of the plurality of candidate therapy options for at least a subset of the set of therapy recipient cohorts; and/or determining a subset of the set of therapy data that characterizes the subset of the plurality of therapy options for the at least a subset of the set of therapy recipient cohorts. Generating the graph may include identifying a plurality of outcome statements comparing a plurality of therapy options from the subset of the set of therapy data and defining a sentiment factor for each of the plurality of outcome statements comparing the plurality of therapy options based upon, at least in part, performing sentiment analysis on the plurality of outcome statements data comparing the plurality of therapy options. Generating the ranked list of the plurality of candidate therapy options may include ranking the plurality of candidate therapy options as one or more of: a most positive therapy option, a least positive therapy option, and one or more moderately positive therapy options. A first comparative assessment for a first therapy option with respect to at least a subset of a set of therapy recipient cohorts may be determined based upon, at least in part, comparing the first therapy option of the plurality of candidate therapy options to a reference therapy option. A second comparative assessment for a second therapy option with respect to the at least a subset of the set of therapy recipient cohorts may be determined based upon, at least in part, comparing the second therapy option of the plurality of candidate therapy options to the reference therapy option. A hierarchical order to the first therapy option and the second therapy option may be assigned to generate the ranking of the plurality of candidate therapy options based upon, at least in part, analyzing the first comparative assessment for the first therapy option and the second comparative assessment for the second therapy option. A sentiment factor conflict may be detected with respect to the plurality of connections between a first therapy option and a second therapy option. Using a set of ranking criteria, the plurality of connections between the first therapy option and the second therapy option may be evaluated. A hierarchical order to the first therapy option and the second therapy option may be assigned to generate the ranking of the subset of therapy options based upon, at least in part, evaluating the plurality of connections between the first and second therapy options.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE SEVERAL VIEWS OF THE DRAWINGS

Like reference symbols in the various drawings indicate like elements.

DETAILED DESCRIPTION

Figure 1:
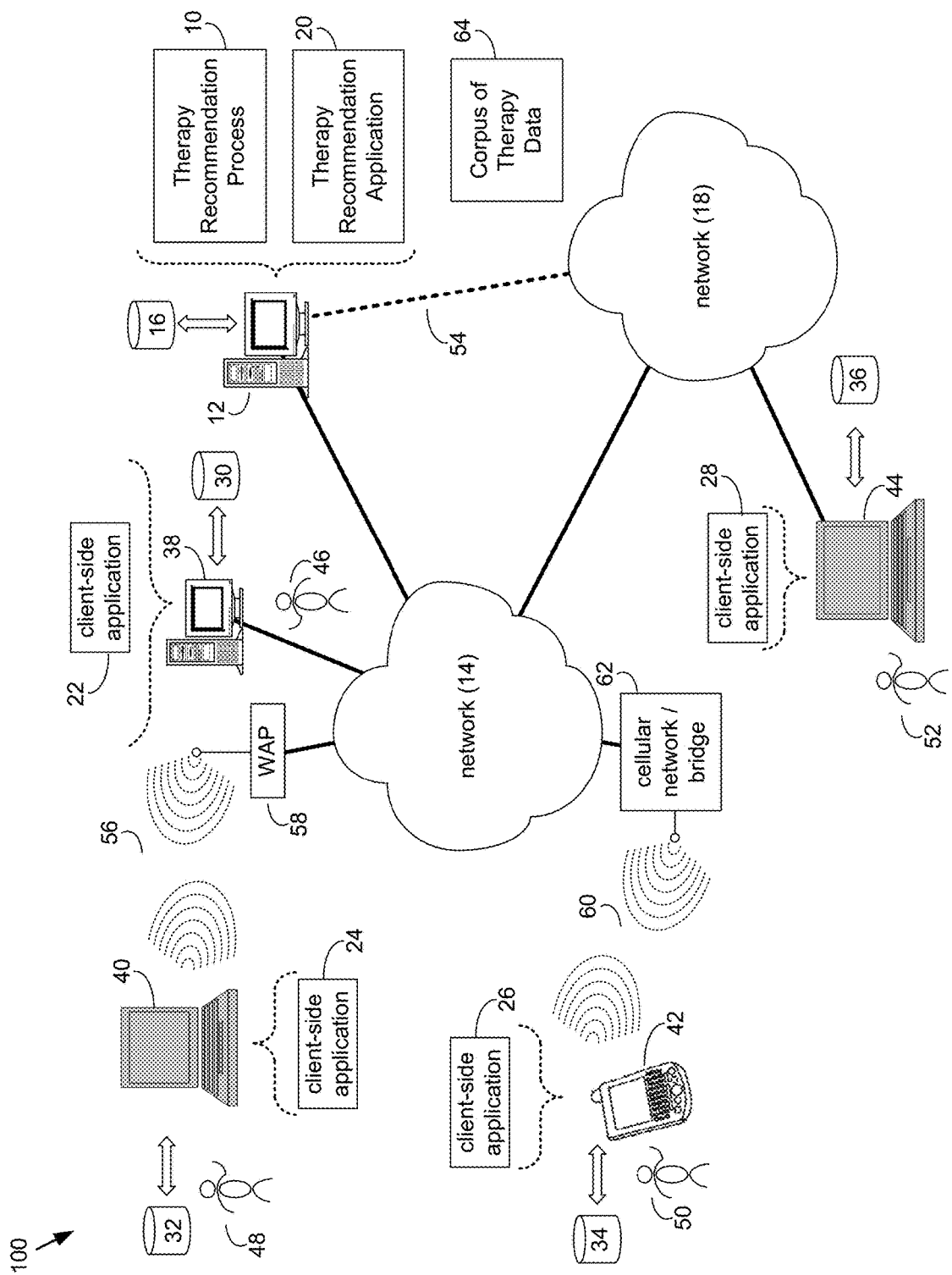
FIG. 1 is an example diagrammatic view of therapy recommendation process coupled to a distributed computing network according to one or more example implementations of the disclosure.
Figure 2:
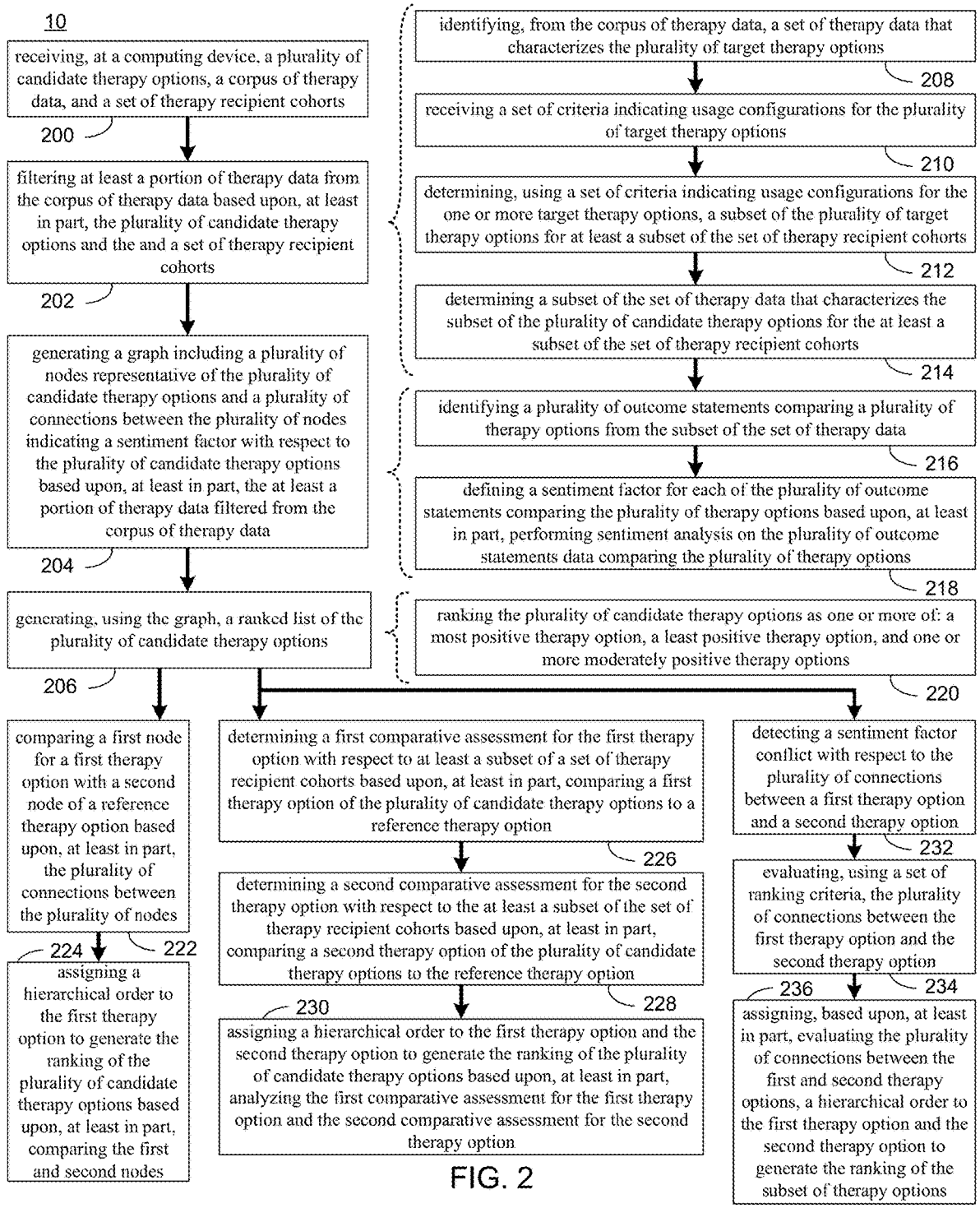
FIG. 2 is an example flowchart of the therapy recommendation process of FIG. 1 according to one or more example implementations of the disclosure.
Figure 3:
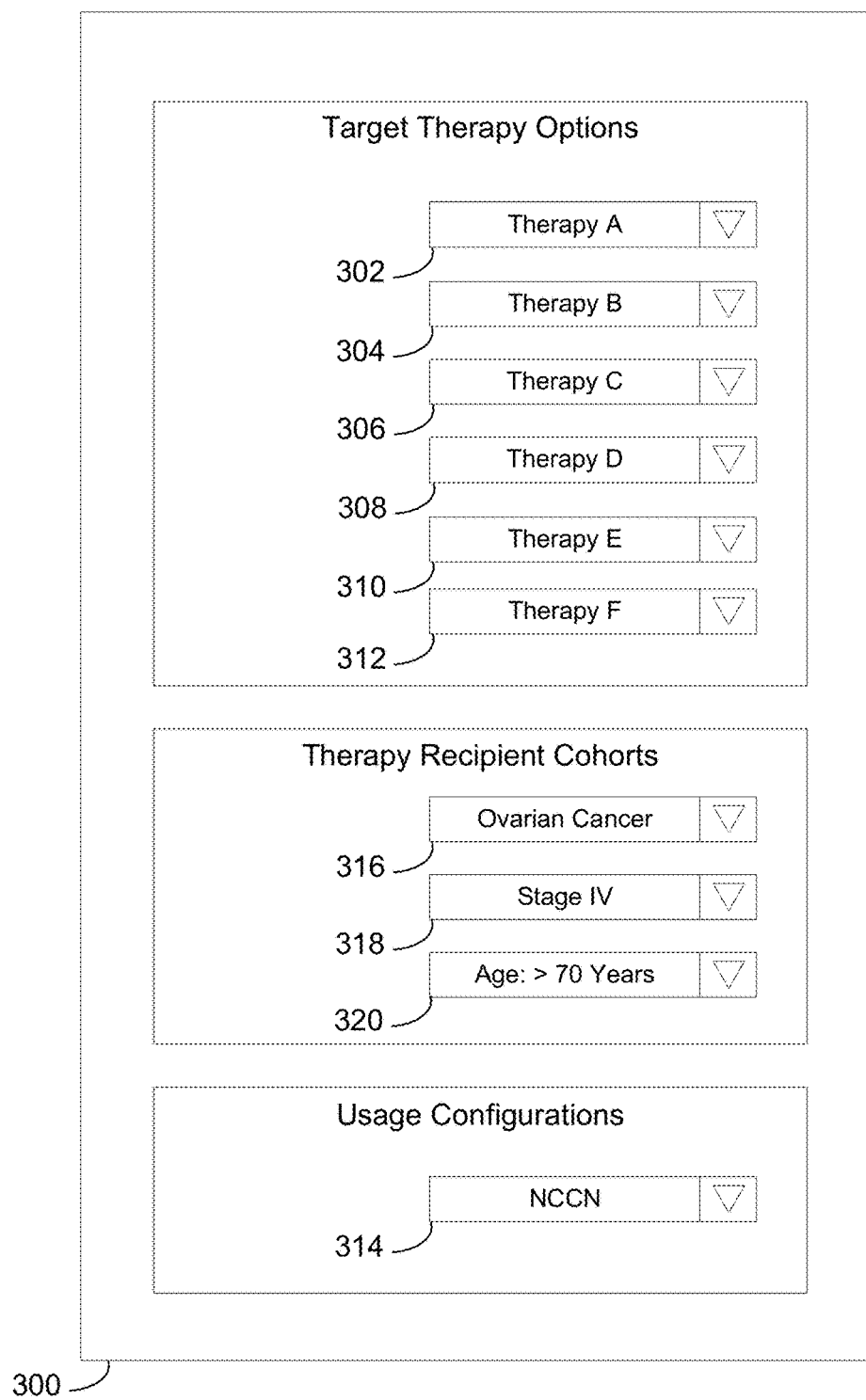
FIG. 3 is an example diagrammatic view of a user interface of the therapy recommendation process of FIG. 1 according to one or more example implementations of the disclosure.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to FIG. 1, there is shown therapy recommendation process 10 that may reside on and may be executed by a computing device 12, which may be connected to a network (e.g., network 14) (e.g., the internet or a local area network). Examples of computing device 12 (and/or one or more of the client electronic devices noted below) may include, but are not limited to, a personal computer(s), a laptop computer(s), mobile computing device(s), a server computer, a series of server computers, a mainframe computer(s), or a computing cloud(s). Computing device 12 may execute an operating system, for example, but not limited to, Microsoft® Windows®; Mac® OS X®; Red Hat® Linux®, or a custom operating system. (Microsoft and Windows are registered trademarks of Microsoft Corporation in the United States, other countries or both; Mac and OS X are registered trademarks of Apple Inc. in the United States, other countries or both; Red Hat is a registered trademark of Red Hat Corporation in the United States, other countries or both; and Linux is a registered trademark of Linus Torvalds in the United States, other countries or both).

As will be discussed below in greater detail, a therapy recommendation process, such as therapy recommendation process 10 of FIG. 1, may receive, at a computing device, a plurality of candidate therapy options, a corpus of therapy data, and a set of therapy recipient cohorts. At least a portion of therapy data may be filtered from the corpus of therapy data based upon, at least in part, the plurality of candidate therapy options and the set of therapy recipient cohorts. A graph may be generated to include a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. Using the graph, a ranked list of the plurality of candidate therapy options may be generated.

The instruction sets and subroutines of therapy recommendation process 10, which may be stored on storage device 16 coupled to computing device 12, may be executed by one or more processors (not shown) and one or more memory architectures (not shown) included within computing device 12. Storage device 16 may include but is not limited to: a hard disk drive; a flash drive, a tape drive; an optical drive; a RAID array; a random access memory (RAM); and a read-only memory (ROM).

Network 14 may be connected to one or more secondary networks (e.g., network 18), examples of which may include but are not limited to: a local area network; a wide area network; or an intranet, for example.

Therapy recommendation process 10 may be a stand-alone application that interfaces with an applet/application that is accessed via client applications 22, 24, 26 and 28. In some embodiments, therapy recommendation process 10 may be, in whole or in part, distributed in a cloud computing topology. In this way, computing device 12 and storage device 16 may refer to multiple devices, which may also be distributed throughout network 14 and/or network 18.

Computing device 12 may execute a therapy recommendation application (e.g., therapy recommendation application 20), examples of which may include, but are not limited to, medical databases, medical diagnostic tools, web-based medical diagnostic tools, etc. One example of a therapy recommendation application may include IBM Watson Health. Therapy recommendation process 10 and/or therapy recommendation application 20 may be accessed via client applications 22, 24, 26 and 28. Therapy recommendation process 10 may be a stand-alone application, or may be an applet/application/script/extension that may interact with and/or be executed within therapy recommendation application 20, a component of therapy recommendation application 20, and/or one or more of client applications 22, 24, 26 and 28. Therapy recommendation application 20 may be a stand-alone application, or may be an applet/application/script/extension that may interact with and/or be executed within therapy recommendation process 10, a component of therapy recommendation process 10, and/or one or more of client applications 22, 24, 26 and 28. One or more of client applications 22, 24, 26 and 28 may be a stand-alone application, or may be an applet/application/script/extension that may interact with and/or be executed within and/or be a component of therapy recommendation process 10 and/or therapy recommendation application 20. Examples of client applications 22, 24, 26 and 28 may include, but are not limited to, applications that receive queries to search for content from one or more databases, servers, cloud storage servers, etc., a textual and/or a graphical user interface, a customized web browser, a plugin, an Application Programming Interface (API), or a custom application. The instruction sets and subroutines of client applications 22, 24, 26 and 28 which may be stored on storage devices 30, 32, 34, 36, coupled to client electronic devices 38, 40, 42, 44, and/or camera system (not shown) may be executed by one or more processors (not shown) and one or more memory architectures (not shown) incorporated into client electronic devices 38, 40, 42, 44.

Storage devices 30, 32, 34, 36, may include but are not limited to: hard disk drives; flash drives, tape drives; optical drives; RAID arrays; random access memories (RAM); and read-only memories (ROM). Examples of client electronic devices 38, 40, 42, 44 (and/or computing device 12) may include, but are not limited to, a personal computer (e.g., client electronic device 38), a laptop computer (e.g., client electronic device 40), a smart/data-enabled, cellular phone (e.g., client electronic device 42), a notebook computer (e.g., client electronic device 44), a tablet (not shown), a server (not shown), a television (not shown), a smart television (not shown), a media (e.g., video, photo, etc.) capturing device (not shown), and a dedicated network device (not shown). Client electronic devices 38, 40, 42, 44 may each execute an operating system, examples of which may include but are not limited to, Microsoft® Windows®; Mac® OS X®; Red Hat® Linux®, Windows® Mobile, Chrome OS™, Blackberry® OS, Fire® OS, or a custom operating system.

One or more of client applications 22, 24, 26 and 28 may be configured to effectuate some or all of the functionality of therapy recommendation process 10 (and vice versa). Accordingly, therapy recommendation process 10 may be a purely server-side application, a purely client-side application, or a hybrid server-side/client-side application that is cooperatively executed by one or more of client applications 22, 24, 26 and 28 and/or therapy recommendation process 10.

One or more of client applications 22, 24, 26, 28, may be configured to effectuate some or all of the functionality of therapy recommendation application 20 (and vice versa). Accordingly, therapy recommendation application 20 may be a purely server-side application, a purely client-side application, or a hybrid server-side/client-side application that is cooperatively executed by one or more of client applications 22, 24, 26, 28 and/or therapy recommendation application 20. As one or more of client applications 22, 24, 26, 28, therapy recommendation process 10, and therapy recommendation application 20, taken singly or in any combination, may effectuate some or all of the same functionality, any description of effectuating such functionality via one or more of client applications 22, 24, 26, 28, therapy recommendation process 10, therapy recommendation application 20, or combination thereof, and any described interaction(s) between one or more of client applications 22, 24, 26, 28, therapy recommendation process 10, therapy recommendation application 20, or combination thereof to effectuate such functionality, should be taken as an example only and not to limit the scope of the disclosure.

Users 46, 48, 50, 52 may access computing device 12 and therapy recommendation process 10 (e.g., using one or more of client electronic devices 38, 40, 42, 44) directly or indirectly through network 14 or through secondary network 18. Further, computing device 12 may be connected to network 14 through secondary network 18, as illustrated with phantom link line 54. Therapy recommendation process 10 may include one or more user interfaces, such as browsers and textual or graphical user interfaces, through which users 46, 48, 50, 52 may access therapy recommendation process 10.

The various client electronic devices may be directly or indirectly coupled to network 14 (or network 18). For example, client electronic device 38 is shown directly coupled to network 14 via a hardwired network connection. Further, client electronic device 44 is shown directly coupled to network 18 via a hardwired network connection. Client electronic device 40 is shown wirelessly coupled to network 14 via wireless communication channel 56 established between client electronic device 40 and wireless access point (i.e., WAP) 58, which is shown directly coupled to network 14. WAP 58 may be, for example, an IEEE 800.11a, 800.11b, 800.11g, Wi-Fi®, and/or Bluetooth® (including Bluetooth® Low Energy) device that is capable of establishing wireless communication channel 56 between client electronic device 40 and WAP 58. Client electronic device 42 is shown wirelessly coupled to network 14 via wireless communication channel 60 established between client electronic device 42 and cellular network/bridge 62, which is shown directly coupled to network 14.

Some or all of the IEEE 800.11x specifications may use Ethernet protocol and carrier sense multiple access with collision avoidance (i.e., CSMA/CA) for path sharing. The various 800.11x specifications may use phase-shift keying (i.e., PSK) modulation or complementary code keying (i.e., CCK) modulation, for example. Bluetooth® (including Bluetooth® Low Energy) is a telecommunications industry specification that allows, e.g., mobile phones, computers, smart phones, and other electronic devices to be interconnected using a short-range wireless connection. Other forms of interconnection (e.g., Near Field Communication (NFC)) may also be used.

As discussed above and referring also at least to FIGS. 2-7, therapy recommendation process 10 may receive 200, at a computing device, a plurality of candidate therapy options, a corpus of therapy data, and a set of therapy recipient cohorts. At least a portion of therapy data may be filtered 202 from the corpus of therapy data based upon, at least in part, the plurality of candidate therapy options and the set of therapy recipient cohorts. A graph may be generated 204 to include a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. Using the graph, a ranked list of the plurality of candidate therapy options may be generated 206.

In some implementations consistent with the present disclosure, systems and methods may be provided for aggregating information captured in a large collection of published articles for the purpose of establishing a purely evidence-based and unbiased ranking of therapies for a specific cohort of patients. Therapy recommendation process 10 may utilize studies that are relevant for the type of patient in question as evidence for therapy ranking purposes (e.g. filtering out results of a study involving a young, vibrant patient cohort when determining best therapy choices for older, more feeble patients). In some implementations, therapy recommendation process 10 may make use of evidence from clinical trials, systematic reviews, and/or other types of studies and uses both findings which compare multiple therapies against each other as well as statements of therapy effectiveness made in a non-comparative context. As will be discussed in greater detail below, therapy recommendation process 10 may give preference to publications resulting from later phase and randomized clinical trials and those which compare the effectiveness of one therapy option versus another. When determining which therapies or therapy options are considered most effective for a given cohort, therapy recommendation process 10 may consider various types of outcomes including effects on patient survival, observed response to therapy, toxicities experienced while on therapy, and/or general impact on patient quality of life.

In some embodiments, therapy recommendation process 10 may provide evidence-based therapy recommendations for patients afflicted with cancer or other, chronic disease types that reflect current known best practice in healthcare and are individualized to account for specific demographic, phenotypic and genomic details of a specific patient. Conventional treatment advisor implementations are often driven by the opinions of a very small number of doctors (e.g., 1-2), where therapies or therapy options are ranked based on the explicit input of those specific physicians. Evidence may be associated with therapy recommendations, but does not play a role in determining what are considered best, next best and not recommended therapies. As such, there are a number of reasons that the conventional implementation may not be ideal. For example, treatment recommendations may be biased towards the specific physicians providing input and may not reflect general consensus of best therapy options for a given disease. The fact that recommendations are not evidence-based has led to a significant number of prospective clients avoiding use of these solutions given lack of agreement with recommendation bias from a given, potentially competing organization. Significant effort may be required to capture physician input relative to how to rank therapies for a given patient cohort which may be repeated on a frequent basis to remain current with latest advances in treatments for a given disease.

In another example, treatment recommendations may not be well substantiated by evidence proving effectiveness of a given therapy for a particular class of patient. Ideally, one would like to associate evidence with a particular therapy that demonstrates effectiveness and good outcomes for patients like the current patient. However, it may be difficult for even an expert physician to keep up with all the published literature comparing effectiveness of therapies for a given disease. For example, there are over 19,000 published articles relevant to therapies considered for ovarian cancer with new articles being published on a daily basis. This may be a daunting task for even the most voracious reader to keep up with, not to mention expert doctors whose schedule is dominated with patient encounters. Accordingly, implementations of therapy recommendation process 10 may provide the ability to derive a preferential view of therapy options for a given therapy recipient/patient cohort that is solely based on the body of published studies evaluating therapy outcomes enables delivery of purely evidence-based treatment advisor solutions that avoid specific physician bias and are able to quickly adapt to the exploding volume of evidence being published on new therapies and their relative effectiveness compared to established therapy options.

In some implementations, therapy recommendation process 10 may receive 200, at a computing device, a plurality of candidate therapy options, a corpus of therapy data, and a set of therapy recipient cohorts. In some implementations, therapy recommendation process 10 may receive a corpus of published articles (e.g., corpus of therapy data 64) to yield a knowledge base of therapy outcomes and therapy outcome comparisons and the cohorts each applies to. The plurality of candidate therapy options may include a set of therapies a user may be interested in ranking. For example, therapy recommendation process 10 may include a user interface configured to receive a selection of a plurality of candidate therapy options. A candidate therapy option may generally include a specified treatment intended to relieve or heal a disorder. Examples of candidate therapy options may include medicinal or drug regimens, applications of chemotherapy drugs (e.g., for cancer patients), surgical procedures, etc. A user may access user interface 300 to select (e.g., via a drop-down menu, searchable menu, search bar, options in the form of selectable button, etc.) a plurality of candidate therapy options (e.g., candidate therapy options 302, 304, 306, 308, 310). In this manner and as will be discussed in greater detail below, the plurality of candidate therapy options may be selected for ranking by therapy recommendation process 10. In some implementations, the plurality of candidate therapy options may include at least two therapy options for ranking.

In some implementations, therapy recommendation process 10 may receive a set of therapy recipient cohorts (e.g., therapy recipient cohorts 316, 318, 320). In some implementation, the set of therapy recipient cohorts may generally include a plurality of characteristics of a patient or potential therapy recipient for whom a ranked list of therapy options may be generated. In some embodiments, the set of recipient therapy cohorts may generally include the age, diagnosis, demographic, phenotypic, and/or genomic details of a patient or a group of therapy recipients. It will be appreciated that various characteristics or attributes may be used within the set of therapy recipient cohorts (e.g., therapy recipient cohorts 316, 318, 320) within the scope of the present disclosure.

Figure 4:
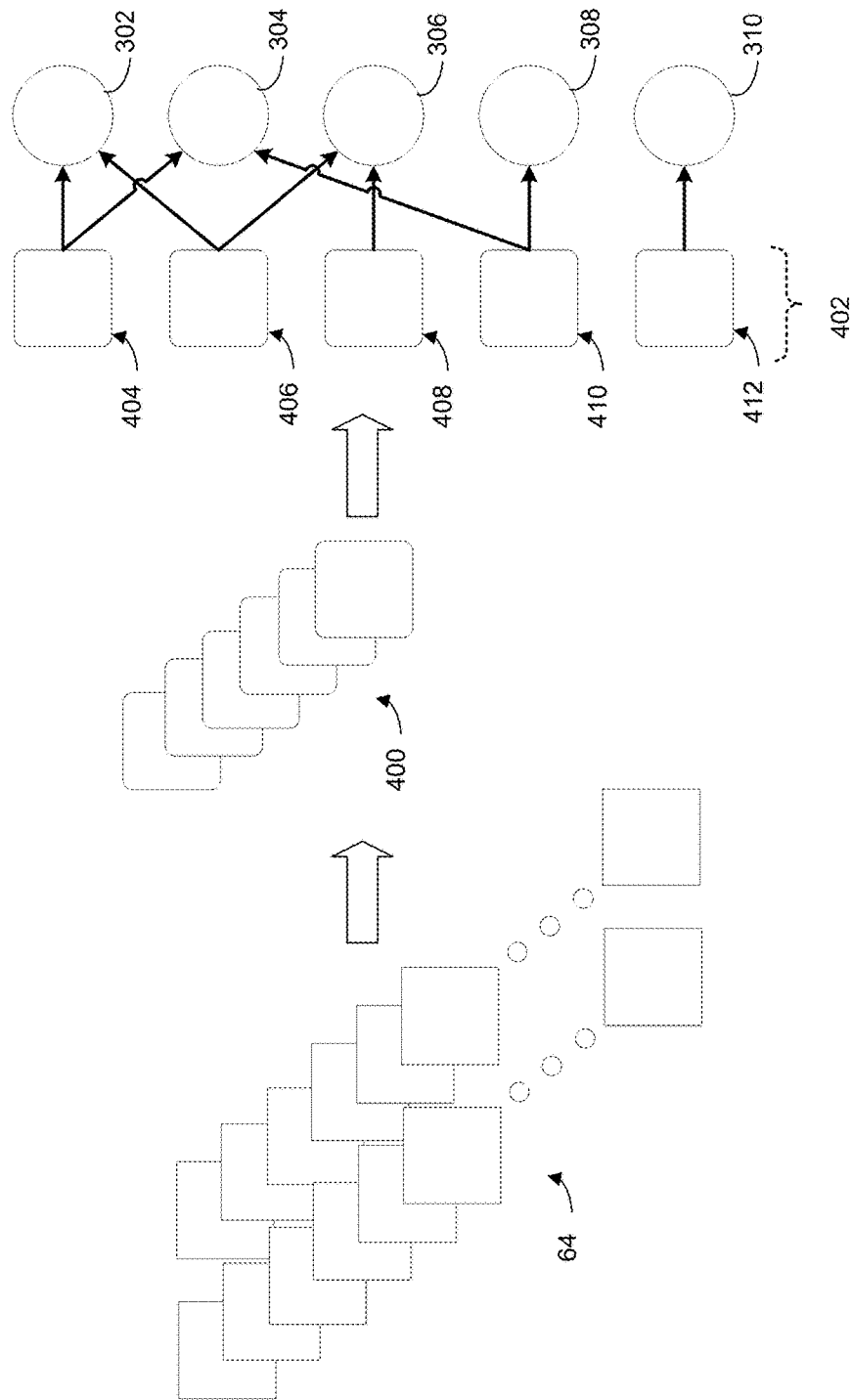
FIG. 4 is an example diagrammatic view of filtering the corpus of therapy data according to one or more example implementations of the disclosure.

Referring also to FIG. 4 and in some implementations, therapy recommendation process 10 may filter 202 at least a portion of therapy data from the corpus of therapy data based upon, at least in part, the plurality of candidate therapy options and the set of therapy recipient cohorts. As discussed above, therapy recommendation process 10 may receive 200 a plurality of candidate therapy options to rank. For example, a user may select a plurality of candidate therapy options (e.g., candidate therapy options 302, 304, 306, 308, 310). In some implementations, therapy recommendation process 10 may process or search the corpus of received 200 therapy data. For example, therapy recommendation process 10 may filter 202 the corpus of therapy data to identify at least a portion of therapy data based upon, at least in part, the plurality of candidate therapy options and the set of therapy recipient cohorts. In some implementations, filtering 202 at least a portion of therapy data from the corpus of therapy data may include identifying 208, from the corpus of therapy data, a set of therapy data that characterizes the plurality of candidate therapy options. For example, therapy recommendation process 10 may identify 208 therapy data (e.g., a plurality of studies 400 that relate to or characterize the plurality of candidate therapy options (e.g., candidate therapy options 302, 304, 306, 308, 310). Therapy recommendation process 10 may query the corpus of therapy data (e.g., corpus of therapy data 64) to identify 208 a set of articles and associated findings involving the plurality of candidate therapy options as well as articles making non-comparative statements regarding the plurality of candidate therapy options. In this manner, therapy recommendation process 10 may identify 208 a sub-corpus of articles and other therapy data (e.g., sub-corpus of therapy data 400) from the received 200 corpus of therapy data (e.g., corpus of therapy data 64).

In some implementations, therapy recommendation process 10 may receive 210 a set of criteria indicating usage configurations for the plurality of candidate therapy options. For example, the set of criteria indicating usage configurations (e.g., usage configurations 314) may generally include criteria identifying when one or more therapy options are relevant. In some implementations, the set of criteria indicating usage configurations may include criteria identifying therapy options from a consensus-based guideline that e.g., National Comprehensive Cancer Network (NCCN) may deem relevant for a given therapy recipient cohort. It will be appreciated that other evidence-based criteria for identifying relevant therapy options may be utilized within the scope of the present disclosure. For example, the set of criteria may be user-defined and may allow a user to select which therapy options are relevant.

In some implementations, therapy recommendation process 10 may filter 202 at least a portion of therapy data from the corpus of therapy data (e.g., corpus of therapy data 64) by determining 212, using the set of criteria indicating usage configurations (e.g., usage configurations 314) for the one or more candidate therapy options and/or a subset of the plurality of candidate therapy options for at least a subset of the set of therapy recipient cohorts (e.g., therapy recipient cohorts 316, 318, 320). For example, suppose therapy recommendation process 10 receives 200 a plurality of candidate therapy options for e.g., ovarian cancer treatment, a corpus of therapy data, and a set of therapy recipient cohorts including e.g., stage IV ovarian cancer patients over 70 years old and a set of usage configurations including e.g., a set of therapy options defined for a set of therapy recipient cohorts. As discussed above and in some implementations, therapy recommendation process 10 may receive 200 the plurality of candidate therapy options and/or the set of therapy recipient cohorts via a user interface (e.g., user interface 300).

In some implementations, therapy recommendation process 10 may filter 202 the at least a portion of the therapy data from the corpus of therapy data by determining 214, based on the subset of the plurality of candidate therapy options, a subset of the set of therapy data that characterizes the subset of the plurality of therapy options for the at least a subset of the set of therapy recipient cohorts. For example, therapy recommendation process 10 may determine the subset of articles or other evidence-based information from the corpus of therapy data that pertain to therapy options that are relevant (e.g., based on the set of criteria indicating usage configurations) and that applies to the set of therapy recipient cohorts. In some implementations, therapy recommendation process 10 may determine 214 a subset (e.g., subset of sub-corpus of therapy data 402) of the set of therapy data (e.g., sub-corpus of therapy data 400) that characterizes the subset of the plurality of therapy options for the at least a subset of the set of therapy recipient cohorts.

For example, the subset of sub-corpus of therapy data 402 may include e.g., five studies or articles (e.g., articles 404, 406, 408, 410, 412) that include comparative outcome statements (as will be discussed in greater detail below) comparing the plurality of candidate therapy options for at least a subset of the set of therapy recipient cohorts.

Continuing with the above example where the candidate therapy options include cancer treatment and the set of therapy recipient cohorts include patients with stage IV ovarian cancer who are over 70 years old, therapy recommendation process 10 may determine 214 a subset of the set of therapy data from studies involving stage IV ovarian cancer patients who are over 70 years old. In some implementations, the subset of the set of therapy data may include evidence from studies specific to ovarian cancer patients.

In some implementations, therapy recommendation process 10 may filter 202 evidence from studies involving stage IV ovarian cancer for patients under 70 from the subset of the set of therapy data. In this manner, therapy recommendation process 10 may filter 202 at least a portion of therapy data from the corpus of therapy data based upon, at least in part, the plurality of candidate therapy options and the set of therapy recipient cohorts. In some implementations, therapy recommendation process 10 may include one or more rules to define which therapy recipient cohorts may be used to filter 202 the at least a portion of therapy data from the corpus of therapy data.

Returning to the above example, therapy recommendation process 10 may filter 202 evidence from studies involving stage IV ovarian cancer for patients under 70 from the subset of the set of therapy data on the basis of the age cohort. For example, the one or more rules may define that therapy data for therapy options conducted on patients with a lower age than the age of the age of the therapy recipient cohort may be filtered 202 out of the ranked list as these therapy options may be more taxing or may even be hazardous on older patients. While a rule regarding age has been discussed, it will be appreciated that other rules for other cohorts may be defined within the scope of the present disclosure.

In some implementations, therapy recommendation process 10 may determine 214 a subset of the set of therapy data that characterizes the subset of the plurality of therapy options for each cohort of the set of therapy recipient cohorts. For example and in some implementations, therapy recommendation process 10 may determine 214 a cohort-specific subset of the set of therapy data that applies to the subset of the plurality of therapy options. Continuing with the above example, therapy recommendation process 10 may determine a subset of the set of therapy data for each therapy recipient cohort (e.g., ovarian cancer, stage IV, age greater than 70 years old, etc.).

Figure 5:
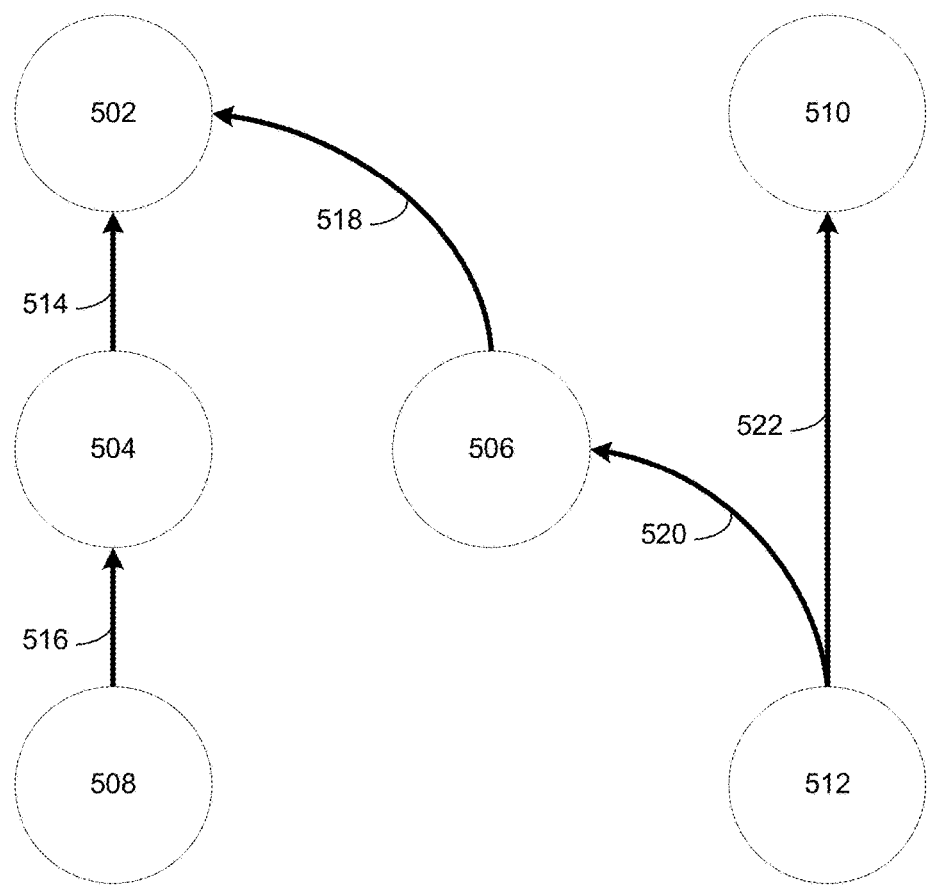
FIGS. 5-6 are example diagrammatic views of graphs of candidate therapy options generated by a therapy recommendation process of FIG. 1 according to one or more example implementations of the disclosure.

In some implementations, therapy recommendation process 10 may generate 204 a graph including a plurality of nodes representative of the plurality of candidate therapy options and a plurality of connections between the plurality of nodes indicating a sentiment factor with respect to the plurality of candidate therapy options based upon, at least in part, the at least a portion of therapy data filtered from the corpus of therapy data. In some implementations and as discussed above, the plurality of candidate therapy options may be described and/or compared in the determined 214 subset of the set of therapy data. From at least the subset of the set of therapy data and as will be discussed in greater detail below, therapy recommendation process 10 may rank the plurality of candidate therapy options. Referring also to FIG. 5, therapy recommendation process 10 may generate 204 the graph (e.g., graph 500) with a plurality of nodes (e.g., nodes 502, 504, 506, 508, 510, 512) representative of the plurality of candidate therapy options (e.g., candidate therapy options 302, 304, 306, 308, 310, 312). In some implementations, therapy recommendation process 10 may generate 204 the graph to include a plurality of connections between the plurality of nodes (e.g., connections 514, 516, 518, 520, 522). In some implementations, the plurality of connections (e.g., connections 514, 516, 518, 520, 522) between the plurality of nodes (e.g., nodes 502, 504, 506, 508, 510, 512) may be indicative of or otherwise represent a sentiment factor with respect to the plurality of candidate therapy options (e.g., candidate therapy options 302, 304, 306, 308, 310, 312).

In some implementations, generating 204 the graph may include identifying 216 a plurality of outcome statements comparing a plurality of therapy options from the subset of the set of therapy data. Returning to the above example where the candidate therapy options include cancer treatment and the set of therapy recipient cohorts include patients with stage IV ovarian cancer who are over 70 years old, therapy recommendation process 10 may filter 202 at least a portion of therapy data (e.g., subset of sub-corpus of therapy data 402) and/or (e.g., sub-corpus of therapy data 400)) from the corpus of therapy data for the set of therapy recipient cohorts and set of criteria indicating usage configurations. As discussed above, therapy recommendation process 10 may determine 214 a subset (e.g., subset of sub-corpus of therapy data 402) of the set of therapy data (e.g., sub-corpus of therapy data 400) that characterizes the subset of the plurality of therapy options for the at least a subset of the set of therapy recipient cohorts. From at least the subset of the set of therapy data, therapy recommendation process 10 may identify 216 a plurality of outcome statements comparing the plurality of candidate therapy options. For example, therapy recommendation process 10 may utilize one or more natural language processing (NLP) algorithms or methodologies to identify 216 the plurality of outcome statements without human intervention. In this manner, therapy recommendation process 10 may automatically identify 216 the plurality of outcome statements comparing the plurality of candidate therapy options.

In some implementations, therapy recommendation process 10 may include performing natural language understanding (NLU) algorithms or methodologies on the determined 214 subset of the set of therapy data that characterizes the subset of the plurality of therapy options for the at least a subset of the set of therapy recipient cohorts. For example, NLU may allow therapy recommendation process 10 to process one or more words or combinations of words (e.g., sentences, lines, paragraphs, etc.) to detect a concept (e.g., concept detection) from an article or other therapy data. In this manner, therapy recommendation process 10 may define the concept of the combination of words to determine if the combination of words describes a comparison between the plurality of candidate therapy options. Additionally, NLU and NLP algorithms or methodologies may include other various rules or configurations for identifying comparative statements in the determined 214 subset of the set of therapy data. For example, suppose the subset of the set of therapy data that characterizes the subset of the plurality of therapy options for the at least a subset of the set of therapy recipient cohorts includes an article that states, in part, "therapy option 300 performs better than therapy option 302 for patients who are over the age of 75." From this example combination of words, therapy recommendation process 10 may define this as a comparative outcome statement. It will be appreciated that different statements in the determined 214 subset of the set of therapy data may be defined as a comparative outcome statement.

In some implementations, generating 204 the graph may include defining 218 a sentiment factor for each of the identified plurality of outcome statements comparing the plurality of therapy options based upon, at least in part, performing sentiment analysis on the plurality of outcome statements data comparing the plurality of therapy options. For example, therapy recommendation process 10 may perform sentiment analysis on the plurality of identified 216 comparative outcome statements to define a sentiment factor. Sentiment analysis may generally include the process of computationally identifying and categorizing opinions expressed in a piece of text, especially in order to determine whether the writer's attitude towards a particular therapy option is positive, negative, or neutral. A sentiment factor may generally include a comparative indication of which therapy option is more favorable than another therapy option. For example, suppose the subset of the set of therapy data that characterizes the subset of the plurality of therapy options for the at least a subset of the set of therapy recipient cohorts includes an article that states, in part, "therapy option 300 performs better than therapy option 302 for patients who are over the age of 75." Therapy recommendation process 10 may define 218 a sentiment factor for the identified 216 comparative outcome statement as therapy option 300 is more positive than therapy option 302 for patients with an age greater than 75 years. It will be appreciated that other sentiment factors may be defined for the same therapy options for different therapy recipient cohorts. For example, while therapy recommendation process 10 may define 218 a sentiment factor for the identified 216 comparative outcome statement as therapy option 300 is more positive than therapy option 302 for patients with an age greater than 75 years, therapy recommendation process 10 may identify 216 a comparative outcome statement that finds "therapy option 306 performs better for female patients with no history of heart disease." From this comparative outcome statement, therapy recommendation process 10 may define 218 a sentiment factor for the identified 216 comparative outcome statement defining that therapy option 306 is more positive than therapy option 304 for patients who are female with no history of heart disease. It will be appreciated that sentiment analysis may indicate that a first therapy option is worse than a second therapy option (e.g., negative sentiment) and/or that the first and second therapy options perform equally well (e.g., neutral sentiment).

Returning to the example of FIG. 4 and in some implementation, therapy recommendation process 10 may identify 216 one or more comparative outcome statements from the subset of the set of therapy data 402. For example, suppose therapy recommendation process 10 identifies 216 from article 404 a comparative outcome statement that candidate therapy option 302 is more favorable than candidate therapy option 304; from article 406 a comparative outcome statement that candidate therapy option 302 is more favorable than candidate therapy option 306; from article 408 comparative outcome statement that candidate therapy option 306 is more favorable than a placebo; from article 410 comparative outcome statement that candidate therapy option 304 is more favorable than candidate therapy option 308; and from article 412 comparative outcome statement that candidate therapy option 310 is more favorable than a placebo and/or therapy option 312.

In some implementations, when there are more than one sentiment statement involved, therapy recommendation process 10 may determine an overall sentiment based on aggregation of all the individual sentiment statements, taking into account influence and relevance of the articles involved. In general, the overall sentiment reflects the prevailing sentiment from the collection of articles comparing a given pair of therapies. In some implementations, where it is ambiguous what prevailing sentiment would be, therapy recommendation process 10 may establish or define a neutral relationship between the two treatment nodes involved.

In some implementations, the sentiment factor may be reflected in the graph (e.g., graph 500) of the plurality of candidate therapy options based upon, at least in part, the plurality of connections between the plurality of nodes. For example, the plurality of connections between the plurality of nodes may indicate the sentiment factor for the comparative outcome statement associated with the plurality of candidate therapy options. In some implementations, the plurality of connections (e.g., connections 514, 516, 518, 520, 522) between the plurality of nodes (e.g., nodes 502, 504, 506, 508, 510, 512) may include an arrow or other graphical indicator to reflect or indicate the sentiment factor between the plurality of nodes. For example, a connection (e.g., connection 514) between a first node (e.g., node 504) to a second node (e.g., node 502) with an arrow pointing from the second node to the first node may indicate that the first candidate therapy option represented by the first node may be a more positive therapy option than the second candidate therapy option represented by the second node. For example, therapy recommendation process 10 may generate 204 the graph with connections directed from less positive to more positive outcome therapies (e.g. arrow is on the treatment exhibiting better outcomes). Other graphical indicators may generally include connection labels (e.g., alphanumerical characters), colors, shapes, symbols, etc. In some implementations, the relative positioning of the plurality of nodes may indicate the sentiment factor associated with the plurality of candidate therapy options represented by the plurality of nodes. For example, more positive outcomes associated with a first therapy option may correlate to a vertical position relative to other nodes. For example, a candidate therapy option with a most positive outcome may be represented by a node positioned higher than the other nodes. A candidate therapy option with a least positive outcome may be represented as the lowest vertical node. In some implementations, a relative horizontal positioning of the plurality of nodes may indicate the sentiment factor associated with the plurality of candidate therapy options represented by the plurality of nodes. For example, a left-most node may represent a candidate therapy option with the least positive outcome and a right-most node may represent a candidate therapy option with a most positive outcome. In some implementations, the left-most node may represent the candidate therapy option with the most positive outcome and the right-most node may represent the candidate therapy option with the least positive outcome. It will be appreciated that other positioning arrangements may be used to represent a sentiment factor associated with the plurality of comparative outcome statements and/or the overall effectiveness of the plurality of candidate therapy options.

In some implementations, therapy recommendation process 10 may generate 206, using the graph, a ranked list of the plurality of candidate therapy options. For example, therapy recommendation process 10 may produce a ranking of therapy options by "walking" the graph generated 204 from evidence (e.g., determined 214 subset of set of therapy data). In some implementations, therapy options may be ranked based on how far removed they are from the best therapy (the therapy options yielding best outcomes) for a given cohort. For example, say therapy recommendation process has evidence (e.g., the determined 214 subset of the set of therapy data that characterizes the plurality of therapy options for at least a subset of the set of therapy recipient cohorts) on e.g., five therapies for a given cohort, (e.g., candidate therapy options 302, 304, 306, 308, 310, 312) and the evidence shows outcomes for candidate therapy option 302 are better than those for candidate therapy option 304 and 306 and the outcomes for candidate therapy option 304 are better than those for candidate therapy option 308. In this example, therapy recommendation process 10 may rank the candidate therapy options in the order of candidate therapy option 302, candidate therapy option 304, candidate therapy option 306, and candidate therapy option 308 (e.g., where candidate therapy option 302 shows the relatively best outcomes and candidate therapy option 308 shows the relatively least positive outcomes).

In some implementations, generating 206 the ranked list of the plurality of candidate therapy options may include ranking 220 the plurality of candidate therapy options as one or more of: a most positive therapy option, a least positive therapy option, and one or more moderately positive therapy options. Returning to the example where the determined 214 subset of the set of therapy data shows outcomes for candidate therapy option 302 are better than those for candidate therapy options 304 and 306 and the outcomes for candidate therapy option 304 are better than those for candidate therapy option 308. In this example, therapy recommendation process 10 may rank 220 candidate therapy option 302 as the most positive therapy option, candidate therapy option 308 as the least positive therapy option, and/or candidate therapy options 304 and 306 as moderately positive therapy options of the plurality of candidate therapy options. It will be appreciated that the ranking may be cohort-specific and/or usage configuration-specific as discussed above.

Referring also to FIG. 5, therapy recommendation process 10 may generate 206 the ranked list (e.g., ranked list 524) of the most positive or most preferred therapy option(s) (i.e., candidate therapy options 302, 310); one or more moderately positive or moderately preferred therapy options (i.e., candidate therapy options 304, 306); and/or the least positive or least preferred therapy option(s) (i.e., candidate therapy options 308, 312) by traversing the graph (e.g., graph 500). For example, therapy recommendation process 10 may traverse the graph to identify one or more nodes with no edges or connections leading away from the node as most preferred or most positive therapy options for the given therapy recipient cohorts (e.g., therapy recipient cohorts 316, 318, 320). Therapy recommendation process 10 may traverse the graph to identify or rank 220 one or more nodes with edges or connections leading away from the node and with edges or continuations leading to the node as moderately positive or preferred candidate therapy options. For example, because node 506 has connections (e.g., connection 518) leading away from node 506 to node 502 and connections (e.g., connection 520) leading to node 506 from node 512, therapy recommendation process 10 may identify or rank 220 node 506 as a moderately positive therapy option for the given therapy recipient cohorts (e.g., therapy recipient cohorts 316, 318, 320). In some implementations, therapy recommendation process 10 may traverse the graph to identify or rank 220 one or more nodes with edges or connections only leaving the node (i.e., no connections leading to the node) as a least preferred or least positive therapy option for the given therapy recipient cohorts (e.g., therapy recipient cohorts 316, 318, 320).

In some implementations, therapy recommendation process 10 may compare 222 a first node representative of a first therapy option with a second node representative of a reference therapy option based upon, at least in part, the plurality of connections (e.g., connections 514, 516, 518, 520, 522) between the plurality of nodes (e.g., nodes 502, 504 506, 508, 510, 512). As discussed above and in some implementations, therapy recommendation process 10 may identify 216 a comparative outcome statement (e.g., comparison statement indicating that a first candidate therapy option performs better than a second candidate therapy option) and may define 218 the sentiment factor associated with the identified comparative statement. In this example, the "reference" therapy option may refer to another candidate therapy option.

In some implementations, therapy recommendation process 10 may assign 224 a hierarchical order to the first therapy option to generate the ranking of the plurality of candidate therapy options based upon, at least in part, comparing the first and second nodes. Returning to the above example involving a first candidate therapy option (e.g., candidate therapy option 302) and a second candidate therapy option (e.g., candidate therapy option 306), therapy recommendation process 10 may generate 204 the graph to include a node representative of candidate therapy option 302 and a node representative of reference therapy option 306 based upon, at least in part, the defined 218 sentiment factor associated with the identified comparative statement. In some implementations, the connection (e.g., connection 518) between the node generated for the first candidate therapy option 302 (e.g., node 502) and the node generated for the second candidate therapy option 306 (e.g., node 506) may indicate the sentiment factor defined 218 for these therapy options (e.g., indicating that candidate therapy option 302 provides a more positive outcome than candidate therapy option 306). In this manner, therapy recommendation process 10 may assign 224 a hierarchical order including a more senior hierarchical position (i.e., more likely to produce a positive outcome) for the first therapy option (e.g., first candidate therapy option) and a less senior positions (i.e., less likely to produce a positive outcome) for the reference therapy option (e.g., second candidate therapy option).

In some implementations and referring also to the example of FIG. 5, therapy recommendation process 10 may allow non-comparative studies to be utilized. For example, a non-comparative study and/or a study involving a placebo or reference therapy option may indicate that effectiveness of the treatment in isolation and/or against a placebo. In this example, the "reference" therapy option may refer to a placebo therapy option (e.g., placebo therapy option 312). As such, evidence in a study and corresponding sentiment that is specific to a single therapy option may be utilized by therapy recommendation process 10 by inferring a reference node (e.g., reference node 512) representative of a placebo therapy option and/or therapy data without a comparison against another therapy option. For example, suppose a study (e.g., a determined 214 subset of the set of therapy data) compares a candidate therapy option against a placebo therapy option. From this study and as discussed above, therapy recommendation process 10 may identify 216 a comparative outcome statement (e.g., comparison statement indicating that candidate therapy option 310 performs better than a placebo therapy option (e.g., placebo therapy option 312)) and may define 218 the sentiment factor associated with the identified comparative statement. In another example, suppose a study discusses evidence about the effectiveness of a therapy options without comparing to another study. Therapy recommendation process 10 may generate a placebo node representative of a placebo therapy and may identify sentiment within the study to generate the sentiment factor associated with the therapy option.

In some implementations, therapy recommendation process 10 may assign 224 a hierarchical order to the first therapy option to generate the ranking of the plurality of candidate therapy options based upon, at least in part, comparing the first and second nodes. Returning to the above example involving candidate therapy option 310 and a placebo therapy option, therapy recommendation process 10 may generate 204 the graph to include a node representative of candidate therapy option 310 (e.g., node 510) and a node representative of reference therapy option (e.g., node 512) based upon, at least in part, the defined 218 sentiment factor associated with the identified comparative statement. In some implementations, the connection (e.g., connection 522) between the node generated for candidate therapy option 310 and the node generated from reference therapy option may indicate the sentiment factor defined 218 for these therapy options (e.g., indicating that candidate therapy option 310 provides a more positive outcome than e.g., a placebo). In this manner, therapy recommendation process 10 may assign 224 a hierarchical order including a more senior hierarchical position (i.e., more likely to produce a positive outcome) for the first therapy option and a less senior positions (i.e., less likely to produce a positive outcome) for the reference therapy.

In some implementations, therapy recommendation process 10 may determine 226 a first comparative assessment for a first therapy option with respect to at least a subset of a set of therapy recipient cohorts based upon, at least in part, comparing the first therapy option of the plurality of candidate therapy options to a reference therapy option. In this example, the "reference" therapy option may refer to another candidate therapy option or a placebo therapy option. As discussed above, therapy recommendation process 10 may identify 216 a comparative outcome statement (e.g., a comparison statement indicating that a first candidate therapy option performs better than a second candidate therapy option) and may define 218 the sentiment factor associated with the identified comparative statement. The first comparative assessment may define the relative hierarchical order of the first candidate therapy option and the reference therapy option.

In some implementations, therapy recommendation process 10 may determine 228 a second comparative assessment for a second therapy option with respect to the at least a subset of the set of therapy recipient cohorts based upon, at least in part, comparing the second therapy option of the plurality of candidate therapy options to the reference therapy option. In this example, the "reference" therapy option may refer to another candidate therapy option or a placebo therapy option. In some implementations, the first and the second candidate therapy options may be compared against the same reference therapy option. As discussed above, therapy recommendation process 10 may identify 216 a comparative outcome statement (e.g., a comparison statement indicating that a first candidate therapy option performs better than a reference candidate therapy option) and may define 218 the sentiment factor associated with the identified comparative statement. The second comparative assessment may define the relative hierarchical order of the second candidate therapy option and the reference therapy option.

In some implementations, therapy recommendation process 10 may assign 230 a hierarchical order to the first therapy option and the second therapy option to generate the ranking of the plurality of candidate therapy options based upon, at least in part, analyzing the first comparative assessment for the first therapy option and the second comparative assessment for the second therapy option. In this manner, therapy recommendation process 10 may take into account indirect comparisons between two therapy options when there is no published evidence showing results of a direct, head-to-head comparison. For example, suppose therapy recommendation process 10 receives evidence from e.g., two trials that pertain to a particular therapy recipient cohort. The first trial may compare a first candidate therapy option (e.g., candidate therapy option 302) and a second candidate therapy option (e.g., candidate therapy option 306) and may conclude that candidate therapy option 302 yields better outcomes than candidate therapy option 306. A second study may compare the second candidate therapy option (e.g., candidate therapy option 306) and a third candidate therapy option (e.g., candidate therapy option 312) and deem candidate therapy option 306 as yielding better outcomes than candidate therapy option 312. In this case, therapy recommendation process 10 may assign a hierarchical order/ranking for the first, second, and third therapy options by utilizing the common, reference candidate therapy option (e.g., candidate therapy option 306) to determine that the first candidate therapy option (e.g., candidate therapy option 302) is a better therapy choice than the third candidate therapy option (e.g., candidate therapy option 312) using a common therapy both were compared to (e.g., candidate therapy option 306).

Figure 6:
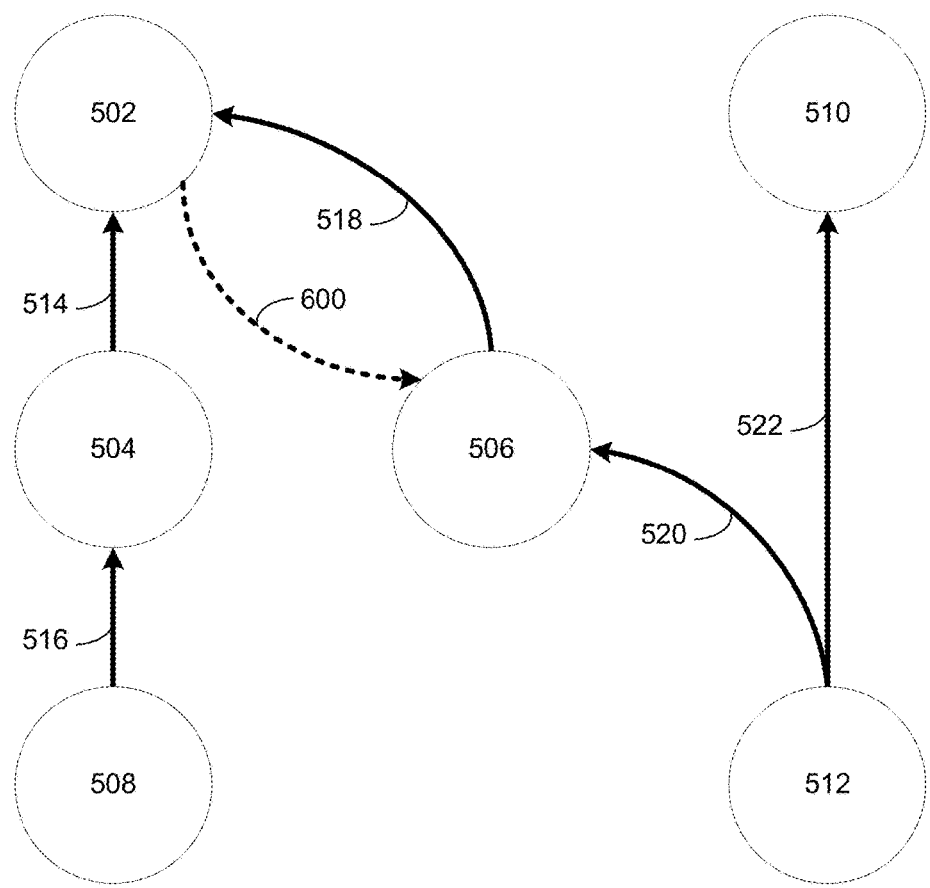

Referring also to the example of FIG. 6 and in some implementations, therapy recommendation process 10 may detect 232 a sentiment factor conflict with respect to the plurality of connections between a first therapy option and a second therapy option. For example, suppose therapy recommendation process 10 determines 214 a subset of the set of therapy data includes two different studies yielding different outcome conclusions for a pair of therapies (e.g., a first study concludes outcomes for candidate therapy option 302 are better than those for candidate therapy option 306, while a second study concludes outcomes for candidate therapy option 306 are better than those for candidate therapy option 302). In some implementations, this inconsistency in sentiment factors may be detected 232 by therapy recommendation process 10 as a sentiment factor conflict. This is represented graphically in FIG. 6 as the dotted connection (e.g., connection 600) between node 502 representative of candidate therapy option 302 and node 506 representative of candidate therapy option 306 and the solid connection (e.g., connection 518) between node 502 representative of candidate therapy option 302 and node 506 representative of candidate therapy option 306.

In some implementations, therapy recommendation process 10 may evaluate 234, using a set of ranking criteria, the plurality of connections between the first therapy option and the second therapy option. The set of ranking criteria may include one or more factors to rank or distinguish therapy data in response to detecting 232 a sentiment factor conflict. For example, the set of ranking criteria may be user-defined (e.g., via a user interface) and/or may be automatically defined by therapy recommendation process 10. The set of ranked criteria may include rules or criteria such as, but not limited to, findings or studies from a later phase trial would take precedence over those from an earlier phase trial; findings or studies from a trial involving randomized controls would take precedence over nonrandomized trials; findings from more recent publications would take precedence over those from older publications; findings from evidence associated with a more specific cohort would take precedence over findings from evidence associated with a less specific cohort (e.g. prefer evidence where the cohort involved were stage IV, ovarian cancer patients over 70 versus evidence where the cohort was less precise (e.g. ovarian cancer patients of all stages and ages)); findings published in a more pre-eminent and cited journal would take precedence over those published in a lesser read and referenced publication, the size of the study involved, where a study with more participants is weighted more than a study with less participants; the rigor of the trial (e.g., a stage III study versus a stage IV study, where latter stage studies are more rigorous), where more rigorous trials would receive a greater weight; degree of precision (e.g., a very broad cohort would be weighted less than a very narrow, specific cohort); etc. While these example criteria have been provided, it will be appreciated that other criteria may be defined for distinguishing a plurality of conflicting outcome statements and/or sentiment factors. In this manner, the plurality of therapy options may be weighted based upon, at least in the part, the ranking criteria.

In some implementations, therapy recommendation process 10 may assign 236, based upon, at least in part, evaluating the plurality of connections between the first and second therapy options, a hierarchical order to the first therapy option and the second therapy option to generate the ranking of the subset of therapy options. In some implementations, therapy recommendation process 10 may define 232 a sentiment factor conflict between two studies, where a first study concludes outcomes for candidate therapy option 302 are better than those for candidate therapy option 306, while a second study concludes outcomes for candidate therapy option 306 are better than those for candidate therapy option 302. In response to detecting 232 this sentiment factor conflict, therapy recommendation process 10 may evaluate 234 candidate therapy option 302 and candidate therapy option 306 based upon, at least in part, the set of ranking criteria. In this example, suppose that the second study finding that candidate therapy option 306 are better than those for candidate therapy option 302 is significantly older (e.g., more than ten years older) than the first study and includes a study population (i.e., number of patients tested) is less than half of the study population of the first study. Because of at least these criteria, therapy recommendation process 10 may weigh the sentiment metric indicating that outcomes for candidate therapy option 302 are better than those for candidate therapy option 306 higher than that of the sentiment metric indicating that outcomes for candidate therapy option 306 are better than those for candidate therapy option 302. In this manner, therapy recommendation process 10 may assign 236 a hierarchical order for the plurality of candidate therapy options by assigning a more senior hierarchical position (i.e., more likely to produce a positive outcome) for the first candidate therapy option (e.g., candidate therapy option 302) and a less senior positions (i.e., less likely to produce a positive outcome) for the second therapy option (e.g., candidate therapy option 306) based upon, at least in part, the weighing the sentiment metric in favor of the sentiment metric indicating that outcomes for candidate therapy option 302 are better than those for candidate therapy option 306.

Figure 7:
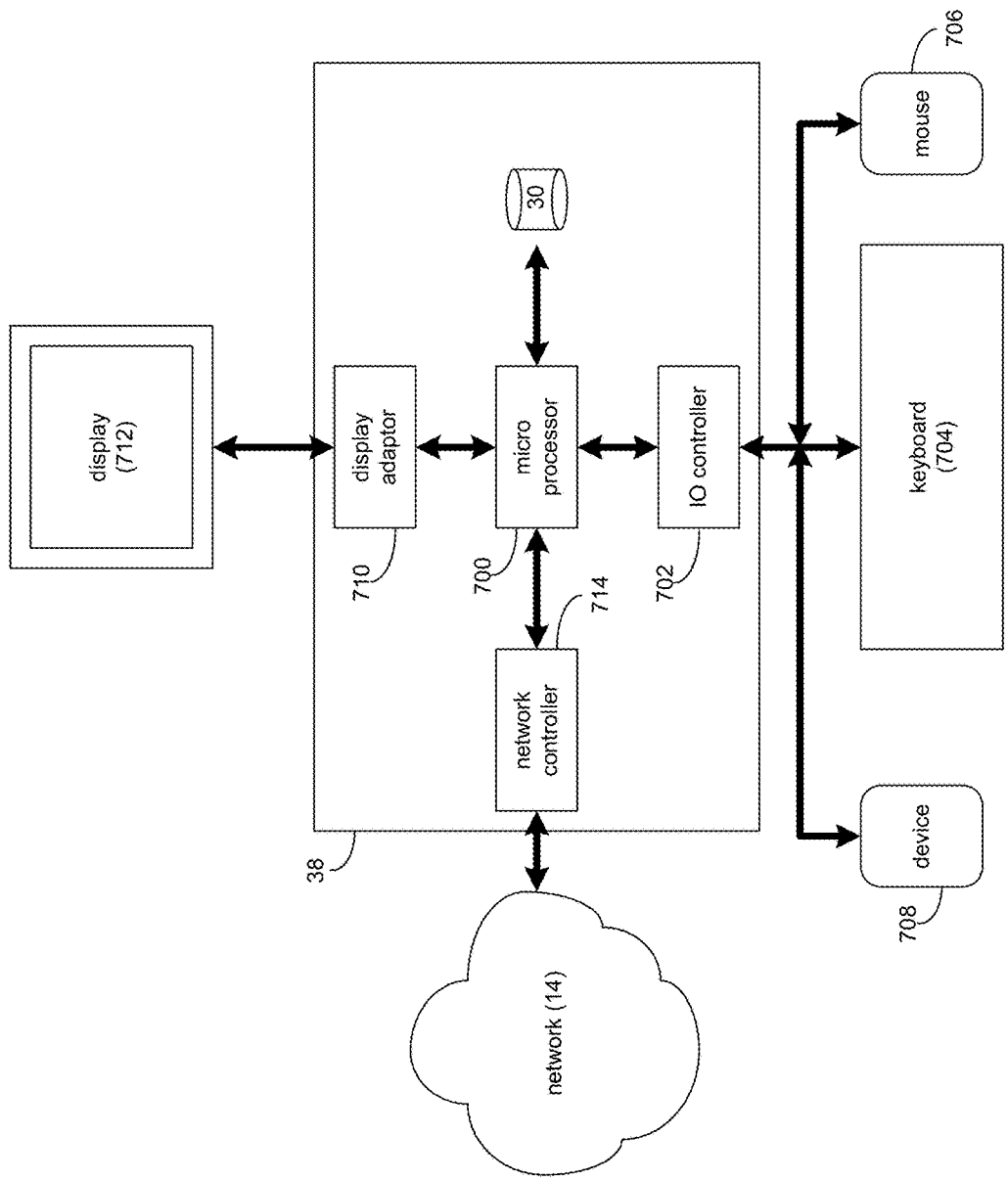
FIG. 7 is an example diagrammatic view of a client electronic device of FIG. 1 according to one or more example implementations of the disclosure.

Referring also to FIG. 7, there is shown a diagrammatic view of client electronic device 38. While client electronic device 38 is shown in this figure, this is for illustrative purposes only and is not intended to be a limitation of this disclosure, as other configurations are possible. For example, any computing device capable of executing, in whole or in part, therapy recommendation process 10 may be substituted for client electronic device 38 within FIG. 7, examples of which may include but are not limited to computing device 12 and/or client electronic devices 40, 42, 44.

Client electronic device 38 may include a processor and/or microprocessor (e.g., microprocessor 700) configured to, e.g., process data and execute the above-noted code/instruction sets and subroutines. Microprocessor 700 may be coupled via a storage adaptor (not shown) to the above-noted storage device(s) (e.g., storage device 30). An I/O controller (e.g., I/O controller 702) may be configured to couple microprocessor 700 with various devices, such as keyboard 704, pointing/selecting device (e.g., mouse 706), custom device, such a microphone (e.g., device 708), USB ports (not shown), and printer ports (not shown). A display adaptor (e.g., display adaptor 710) may be configured to couple display 712 (e.g., CRT or LCD monitor(s)) with microprocessor 700, while network controller/adaptor 714 (e.g., an Ethernet adaptor) may be configured to couple microprocessor 700 to the above-noted network 14 (e.g., the Internet or a local area network).

The terminology used herein is for the purpose of describing particular implementations only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

The corresponding structures, materials, acts, and equivalents of all means or step plus function elements that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to best explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. A computer-implemented method comprising:
    receiving, at a computing device, a corpus of therapy data comprising over 19,000 published articles;
    filtering, concurrently with receiving the corpus of therapy data, the corpus of therapy data based on a set of therapy recipient cohorts, wherein filtering comprises:
        identifying a sub-corpus set of therapy data, receiving a set of criteria indicating usage configurations associated with the sub-corpus set of therapy data, and determining a plurality of candidate therapy options from the sub-corpus set of therapy data which characterizes a plurality of candidate therapy options data;

generating a graph including a plurality of nodes representative of the plurality of candidate therapy options and a plurality of connections between the plurality of nodes indicating a sentiment factor with respect to the plurality of candidate therapy options based upon, at least in part, the sub-corpus set of therapy data filtered from the corpus of therapy data, wherein each of the plurality of connections comprise a more senior hierarchical position on the graph to a first node of the plurality of nodes of a first candidate therapy option of the plurality of candidate therapy options which is more likely to produce a positive outcome and a second less senior position to a second node of the plurality of nodes of a second candidate therapy option of the plurality of candidate therapy options comparatively less likely to produce a positive outcome;

traversing the graph to identify a node with no edges or connections leading away from the node as a most preferred or a most positive therapy option for a given therapy recipient cohort, wherein the node with the most preferred or most positive therapy option is at the most senior hierarchical position on the graph; and generating, using the graph and the traversing, a ranked list of the plurality of candidate therapy options based on a number of connections of the plurality of connections walked through when traversing the graph between the most positive therapy option and each associated therapy option of the plurality of candidate therapy options.

2. The computer-implemented method of claim 1, wherein filtering further comprises:

identifying, from the corpus of therapy data, a set of therapy data that characterizes the plurality of candidate therapy options;

receiving a set of criteria indicating usage configurations for the plurality of candidate therapy options;

determining, using a set of criteria indicating usage configurations for the plurality of candidate therapy options, a subset of the plurality of candidate therapy options for at least a subset of the set of therapy recipient cohorts; and determining a subset of the set of therapy data that characterizes the subset of the plurality of candidate therapy options for the at least a subset of the set of therapy recipient cohorts.

3. The computer-implemented method of claim 2, wherein generating the graph includes:

identifying a plurality of outcome statements comparing a plurality of therapy options from the subset of the set of therapy data; and defining a sentiment factor for each of the plurality of outcome statements comparing the plurality of therapy options based upon, at least in part, performing sentiment analysis on the plurality of outcome statements comparing the plurality of therapy options.

4. The computer-implemented method of claim 1, wherein generating the ranked list of the plurality of candidate therapy options includes ranking the plurality of candidate therapy options as one or more of: a most positive therapy option, a least positive therapy option, and one or more moderately positive therapy options.

5. The computer-implemented method of claim 1, further comprising:

comparing a first node for a first therapy option with a second node of a reference therapy option based upon, at least in part, the plurality of connections between the plurality of nodes; and assigning a hierarchical order to the first therapy option to generate a ranking of the plurality of candidate therapy options based upon, at least in part, comparing the first and second nodes.

6. The computer-implemented method of claim 1, further comprising:

determining a first comparative assessment for a first therapy option with respect to at least a subset of a set of therapy recipient cohorts based upon, at least in part, comparing the first therapy option of the plurality of candidate therapy options to a reference therapy option;

determining a second comparative assessment for a second therapy option with respect to the at least a subset of the set of therapy recipient cohorts based upon, at least in part, comparing the second therapy option of the plurality of candidate therapy options to the reference therapy option; and assigning a hierarchical order to the first therapy option and the second therapy option to generate a ranking of the plurality of candidate therapy options based upon, at least in part, analyzing the first comparative assessment for the first therapy option and the second comparative assessment for the second therapy option.

7. The computer-implemented method of claim 1, further comprising:

detecting a sentiment factor conflict with respect to the plurality of connections between a first therapy option and a second therapy option;

evaluating, using a set of ranking criteria, the plurality of connections between the first therapy option and the second therapy option; and assigning, based upon, at least in part, evaluating the plurality of connections between the first and second therapy options, a hierarchical order to the first therapy option and the second therapy option to generate a ranking of a subset of therapy options.

8. A computer program product comprising a non-transitory computer readable storage medium having a plurality of instructions stored thereon, which, when executed by a processor, cause the processor to perform operations comprising:

receiving, at a computing device, a corpus of therapy data comprising over 19,000 published articles;

filtering, concurrently with receiving the corpus of therapy data, the corpus of therapy data based on a set of therapy recipient cohorts, wherein filtering comprises:

identifying a sub-corpus set of therapy data, receiving a set of criteria indicating usage configurations associated with the sub-corpus set of therapy data, and determining a plurality of candidate therapy options from the sub-corpus set of therapy data which characterizes a plurality of candidate therapy options data;

generating a graph including a plurality of nodes representative of the plurality of candidate therapy options and a plurality of connections between the plurality of nodes indicating a sentiment factor with respect to the plurality of candidate therapy options based upon, at least in part, the sub-corpus set of therapy data filtered from the corpus of therapy data, wherein each of the plurality of connections comprise a more senior hierarchical position on the graph to a first node of the plurality of nodes of a first candidate therapy option of the plurality of candidate therapy options which is more likely to produce a positive outcome and a second less senior position to a second node of the plurality of nodes of a second candidate therapy option of the plurality of candidate therapy options comparatively less likely to produce a positive outcome;

traversing the graph to identify a node with no edges or connections leading away from the node as a most preferred or a most positive therapy option for a given therapy recipient cohort, wherein the node with the most preferred or most positive therapy option is at the most senior hierarchical position on the graph; and generating, using the graph and the traversing, a ranked list of the plurality of candidate therapy options based on a number of connections of the plurality of connections walked through when traversing the graph between the most positive therapy option and each associated therapy option of the plurality of candidate therapy options.

9. The computer program product of claim 8, wherein filtering further comprises:

identifying, from the corpus of therapy data, a set of therapy data that characterizes the plurality of candidate therapy options;

receiving a set of criteria indicating usage configurations for the plurality of candidate therapy options;

determining, using a set of criteria indicating usage configurations for the plurality of candidate therapy options, a subset of the plurality of candidate therapy options for at least a subset of the set of therapy recipient cohorts; and determining a subset of the set of therapy data that characterizes the subset of the plurality of candidate therapy options for the at least a subset of the set of therapy recipient cohorts.

10. The computer program product of claim 9, wherein generating the graph includes:

identifying a plurality of outcome statements comparing a plurality of therapy options from the subset of the set of therapy data; and defining a sentiment factor for each of the plurality of outcome statements comparing the plurality of therapy options based upon, at least in part, performing sentiment analysis on the plurality of outcome statements comparing the plurality of therapy options.

11. The computer program product of claim 8, wherein generating the ranked list of the plurality of candidate therapy options includes ranking the plurality of candidate therapy options as one or more of: a most positive therapy option, a least positive therapy option, and one or more moderately positive therapy options.

12. The computer program product of claim 8, further comprising instructions for:

comparing a first node for a first therapy option with a second node of a reference therapy option based upon, at least in part, the plurality of connections between the plurality of nodes; and assigning a hierarchical order to the first therapy option to generate a ranking of the plurality of candidate therapy options based upon, at least in part, comparing the first and second nodes.

13. The computer program product of claim 8, further comprising instructions for:

determining a first comparative assessment for a first therapy option with respect to at least a subset of a set of therapy recipient cohorts based upon, at least in part, comparing the first therapy option of the plurality of candidate therapy options to a reference therapy option;

determining a second comparative assessment for a second therapy option with respect to the at least a subset of the set of therapy recipient cohorts based upon, at least in part, comparing the second therapy option of the plurality of candidate therapy options to the reference therapy option; and assigning a hierarchical order to the first therapy option and the second therapy option to generate a ranking of the plurality of candidate therapy options based upon, at least in part, analyzing the first comparative assessment for the first therapy option and the second comparative assessment for the second therapy option.

14. The computer program product of claim 8, further comprising instructions for:

detecting a sentiment factor conflict with respect to the plurality of connections between a first therapy option and a second therapy option;

evaluating, using a set of ranking criteria, the first therapy option and the second therapy option; and assigning, based upon, at least in part, evaluating the first and second therapy options, a hierarchical order to the first therapy option and the second therapy option to generate a ranking of a subset of therapy options.

15. A computing system including one or more processors and one or more memories configured to perform operations comprising:

receiving, at a computing device, a corpus of therapy data comprising over 19,000 published articles;

filtering, concurrently with receiving the corpus of therapy data, the corpus of therapy data based on a set of therapy recipient cohorts, wherein filtering comprises:

identifying a sub-corpus set of therapy data, receiving a set of criteria indicating usage configurations associated with the sub-corpus set of therapy data, and determining a plurality of candidate therapy options from the sub-corpus set of therapy data which characterizes a plurality of candidate therapy options data;

generating a graph including a plurality of nodes representative of the plurality of candidate therapy options and a plurality of connections between the plurality of nodes indicating a sentiment factor with respect to the plurality of candidate therapy options based upon, at least in part, the sub-corpus set of therapy data filtered from the corpus of therapy data, wherein each of the plurality of connections comprise a more senior hierarchical position on the graph to a first node of the plurality of nodes of a first candidate therapy option of the plurality of candidate therapy options which is more likely to produce a positive outcome and a second less senior position to a second node of the plurality of nodes of a second candidate therapy option of the plurality of candidate therapy options comparatively less likely to produce a positive outcome;

traversing the graph to identify a node with no edges or connections leading away from the node as a most preferred or a most positive therapy option for a given therapy recipient cohort, wherein the node with the most preferred or most positive therapy option is at the most senior hierarchical position on the graph; and generating, using the graph and the traversing, a ranked list of the plurality of candidate therapy options based on a number of connections of the plurality of connections walked through when traversing the graph between the most positive therapy option and each associated therapy option of the plurality of candidate therapy options.

16. The computing system of claim 15, wherein filtering further comprises:

identifying, from the corpus of therapy data, a set of therapy data that characterizes the plurality of candidate therapy options;

receiving a set of criteria indicating usage configurations for the plurality of candidate therapy options;

determining, using a set of criteria indicating usage configurations for the plurality of candidate therapy options, a subset of the plurality of candidate therapy options for at least a subset of the set of therapy recipient cohorts; and determining a subset of the set of therapy data that characterizes the subset of the plurality of candidate therapy options for the at least a subset of the set of therapy recipient cohorts.

17. The computing system of claim 16, wherein generating the graph includes:

identifying a plurality of outcome statements comparing a plurality of therapy options from the subset of the set of therapy data; and defining a sentiment factor for each of the plurality of outcome statements comparing the plurality of therapy options based upon, at least in part, performing sentiment analysis on the plurality of outcome statements comparing the plurality of therapy options.

18. The computing system of claim 15, wherein generating the ranked list of the plurality of candidate therapy options includes ranking the plurality of candidate therapy options as one or more of: a most positive therapy option, a least positive therapy option, and one or more moderately positive therapy options.

19. The computing system of claim 15, wherein the operations further comprise:

comparing a first node for a first therapy option with a second node of a reference therapy option based upon, at least in part, the plurality of connections between the plurality of nodes; and assigning a hierarchical order to the first therapy option to generate a ranking of the plurality of candidate therapy options based upon, at least in part, comparing the first and second nodes.

20. The computing system of claim 15, wherein the operations further comprise:

determining a first comparative assessment for a first therapy option with respect to at least a subset of a set of therapy recipient cohorts based upon, at least in part, comparing the first therapy option of the plurality of candidate therapy options to a reference therapy option;

determining a second comparative assessment for a second therapy option with respect to the at least a subset of the set of therapy recipient cohorts based upon, at least in part, comparing the second therapy option of the plurality of candidate therapy options to the reference therapy option; and assigning a hierarchical order to the first therapy option and the second therapy option to generate the ranking of the plurality of candidate therapy options based upon, at least in part, analyzing the first comparative assessment for the first therapy option and the second comparative assessment for the second therapy option.

* * * * *